United States Patent
Gatenholm et al.

(10) Patent No.: US 11,648,336 B2
(45) Date of Patent: May 16, 2023

(54) PREPARATION AND APPLICATIONS OF 3D BIOPRINTING BIOINKS FOR REPAIR OF BONE DEFECTS, BASED ON CELLULOSE NANOFIBRILS HYDROGELS WITH NATURAL OR SYNTHETIC CALCIUM PHOSPHATE PARTICLES

(71) Applicant: Cellink Bioprinting AB, Gothenburg (SE)

(72) Inventors: Paul Gatenholm, Riner, VA (US); Hector Martinez, Gothenburg (SE); Michela Schettino, Sperone (IT); Erik Gatenholm, Gothenburg (SE)

(73) Assignee: Cellink Bioprinting AB, Gothenburg (SE)

( * ) Notice: Subject to any disclaimer, the term of this patent is extended or adjusted under 35 U.S.C. 154(b) by 0 days.

(21) Appl. No.: 16/345,363

(22) PCT Filed: Oct. 27, 2017

(86) PCT No.: PCT/EP2017/077669
§ 371 (c)(1),
(2) Date: Apr. 26, 2019

(87) PCT Pub. No.: WO2018/078130
PCT Pub. Date: May 3, 2018

(65) Prior Publication Data
US 2019/0307923 A1 Oct. 10, 2019

Related U.S. Application Data

(60) Provisional application No. 62/414,193, filed on Oct. 28, 2016.

(30) Foreign Application Priority Data

Oct. 28, 2016 (SE) .................................. 1651422-6

(51) Int. Cl.
*A61L 27/46* (2006.01)
*B33Y 10/00* (2015.01)
(Continued)

(52) U.S. Cl.
CPC ........... *A61L 27/46* (2013.01); *A61L 27/3821* (2013.01); *A61L 27/3834* (2013.01);
(Continued)

(58) Field of Classification Search
CPC .. A61L 27/46; A61L 27/3821; A61L 27/3834; A61L 27/3847; A61L 27/3865;
(Continued)

(56) References Cited

U.S. PATENT DOCUMENTS

| 8,147,860 B2 | 4/2012 | Rosenberg et al. |
| 2010/0015447 A1 | 1/2010 | Lahann et al. |

(Continued)

FOREIGN PATENT DOCUMENTS

| CN | 103285427 A | 9/2013 |
| CN | 103285427 B | 11/2014 |
| WO | WO 2016/100856 A1 | 6/2016 |

OTHER PUBLICATIONS

Markstedt, Kajsa, et al., Biomacromolecules 2015, 16, pp. 1489-1496 (Year: 2015).*
Yeo, MyungGu, et al., Biomacromolecules 2011, 12, pp. 502-510 (Year: 2011).*
Chia, Helena N., et al., Journal of Biological Engineering (2015) 9:4, pp. 1-14 (Year: 2015).*
Nakagawa et al (Journal of Nanomaterials, 2013, vol. 2013, pp. 1-13) (Year: 2013).*

(Continued)

*Primary Examiner* — Mark V Stevens
(74) *Attorney, Agent, or Firm* — McCarter & English, LLP (57) ABSTRACT

The present invention relates to preparation of bioink composed of cellulose nanofibril hydrogel with native or synthetic Calcium containing particles. The concentration of the calcium containing particles can be between 1% and 40% w/v. Such bioink can be 3D Bioprinted with or without human or animal cells. Coaxial needle can be used where cellulose nanofibril hydrogel filled with Calcium particles can be used as shell and another hydrogel based bioink mixed with cells can be used as core or opposite. Such 3D Bioprinted constructs exhibit high porosity due to shear thinning properties of cellulose nanofibrils which provides excellent printing fidelity. They also have excellent mechanical properties and are easily handled as large constructs for patient-specific bone cavities which need to be repaired. The porosity promotes vascularization which is crucial for oxygen and nutrient supply. The porosity also makes it possible for further recruitment of cells which accelerate bone healing process. Calcium containing particles can be isolated from autologous bone, allogenic bone or xenogeneic bone but can be also isolated from minerals or be prepared by synthesis. Preferable Calcium containing particles consist of β-tricalcium phosphate which is resorbable or natural bone powder, preferably of human or porcine origin. The particles described in the present invention have particle size smaller than 400 microns, or more preferably smaller than 200 microns, to make it possible to handle in printing nozzle without clogging and to obtain a good resolution. Cellulose nanofibrils can be produced by bacteria orbe isolated from plants. They can be neutral, charged or oxidized to be biodegradable. The bioink can be additionally supplemented by other biopolymers which provide cross-linking. Such biopolymers can be alginates, chitosans, modified hyaluronic acid or modified collagen derived biopolymers.

21 Claims, 4 Drawing Sheets

(51) Int. Cl.
| | |
|---|---|
| *B33Y 80/00* | (2015.01) |
| *A61L 27/38* | (2006.01) |
| *A61L 27/44* | (2006.01) |
| *A61L 27/48* | (2006.01) |
| *A61L 27/52* | (2006.01) |
| *C12N 5/077* | (2010.01) |
| *B29C 64/106* | (2017.01) |
| *B29C 64/165* | (2017.01) |
| *B33Y 70/10* | (2020.01) |

(52) U.S. Cl.
CPC ....... *A61L 27/3847* (2013.01); *A61L 27/3865* (2013.01); *A61L 27/3895* (2013.01); *A61L 27/446* (2013.01); *A61L 27/48* (2013.01); *A61L 27/52* (2013.01); *B29C 64/106* (2017.08); *B29C 64/165* (2017.08); *B33Y 10/00* (2014.12); *B33Y 70/10* (2020.01); *B33Y 80/00* (2014.12); *C12N 5/0654* (2013.01); *A61L 2400/12* (2013.01); *A61L 2430/02* (2013.01); *A61L 2430/12* (2013.01); *C12N 2506/1346* (2013.01); *C12N 2506/45* (2013.01)

(58) Field of Classification Search
CPC ......... B33Y 10/00; B33Y 70/10; B33Y 80/10; C12N 5/0654
See application file for complete search history.

(56) References Cited

U.S. PATENT DOCUMENTS

| | | | | |
|---|---|---|---|---|
| 2012/0190078 | A1* | 7/2012 | Gatenholm | C12N 11/12 435/101 |
| 2014/0038275 | A1* | 2/2014 | Gatenholm | C12M 25/14 435/288.4 |
| 2015/0150681 | A1* | 6/2015 | Ricci | A61F 2/2875 623/23.51 |
| 2015/0231304 | A1 | 8/2015 | Eftekhari | |

OTHER PUBLICATIONS

Sukul et al (European Polymer Journal, Oct. 19, 2015, vol. 73, pp. 308-323) (Year: 2015).*
Franco et al (Acta Biomaterials, 2010, vol. 6, pp. 218-228) (Year: 2010).*
Armstrong et al. (Advanced Healthcare Materials, Apr. 2016, vol. 5, pp. 1724-1730) (Year: 2016).*
Li et al. (Abstract, Rheological properties and 3d printability of alginate-based hydrogels for biofabrication, 10th World Biomaterials Congress, Montreal, Canada, published Mar. 2016) (Year: 2016).*
Armstrong et al. (Advanced Healthcare Materials, Apr. 2016, vol. 5, pp. 1724-1730; evidence of Apr. 2016 date) (Year: 2016).*
International Search Report and Written Opinion, prepared by the European Patent Office, acting as the International Searching Authority, for corresponding international application PCT/EP2017/077669 dated Jan. 22, 2018.
Swedish Search Report prepared by Swedish Patent Office for priority application SE 1651422-6, dated Jun. 1, 2017.
Fernandes, Emanuel M. et al.: "Bionanocomposites from lignocellulosic resources: Properties, applications and future trends for their use in the biomedical field", *Progress in Polymer Science*, vol. 38, (2013), pp. 1415-1441.
Duarte, Eden B. et al.: "Production of hydroxyapatite-bacterial cellulose nanocomposites from agroindustrial wastes", *Cellulose*, vol. 22, (2015), pp. 3177-3187.
Hutchens, Stacy A. et al.: "Biomimetic synthesis of calcium-deficient hydroxyapatite in a natural hydrogel", *Biomaterials*, vol. 27, (2006), pp. 4661-4670.
Leventis, Minas D. et al.: "Minimally Invasive Alveolar Ridge Preservation Utilizing an In Situ Hardening β-Tricalcium Phosphate Bone Substitute: A Multicenter Case Series", *International Journal of Dentistry*, vol. 2016 (2016), Article ID 5406736, pp. 1-12.
Horowitz, Robert A. et al.: "β-tricalcium phosphate as bone substitute material: properties and clinical applications", *Journal of Osseointegration*, vol. 2, No. 2, Jun. 2010, pp. 61-68.
Weinand, Christian et al.: "Hydrogel-β-TCP scaffolds and stem cells for tissue engineering bone", *Bone*, 38, 2006, pp. 555-563.
Martinez Avila, Hector et al.: "Biocompatibility evaluation of densified bacterial nanocellulose hydrogel as an implant material for auricular cartilage regeneration", *Applied Microbiology and Biotechnology*, 2014, 98, pp. 7423-7435, © Springer-Verlag Berlin Heidelberg 2014.
Thoma, Achilleas et al.: "Oromandibular Reconstruction After Cancer Resection", *Clinics in Plastic Surgery*, 32, 2005, pp. 361-375.
Kang, Hyun-Wook et al.: "A 3D bioprinting system to produce human-scale tissue constructs with structural integrity", *Nature Biotechnology*, 34(3), 2016, pp. 312-319.
Fedeorovich, Natalja E. et al.: "Three-Dimensional Fiber Deposition of Cell-Laden, Viable, Patterned Constructs for Bone Tissue Printing", *Tissue Engineering: Part A*, vol. 14, No. 1, 2008, pp. 127-133.
Cancer Research UK: "Head and neck cancers statistics", obtained Aug. 10, 2021 from https://www.cancerresearchuk.org/health-professional/cancer-statistics/statistics-by-cancer-type/head-and-neck-cancer, pp. 1-7.
Hospodiuk, M. et al.: "The bioink: A comprehensive review on bioprintable materials", *Biotechnology Advances*, vol. 35, Issue 2, Mar.-Apr. 2017, pp. 217-239. Manuscript version is provided herein.

* cited by examiner

PREPARATION AND APPLICATIONS OF 3D BIOPRINTING BIOINKS FOR REPAIR OF BONE DEFECTS, BASED ON CELLULOSE NANOFIBRILS HYDROGELS WITH NATURAL OR SYNTHETIC CALCIUM PHOSPHATE PARTICLES

CROSS-REFERENCE TO RELATED APPLICATIONS

This application is the National Stage entry under 35 U.S.C. § 371 of International Application Number PCT/EP2017/077669 filed on Oct. 27, 2017, published on May 3, 2018 under publication number WO 2018/078130 A1, which claims the benefit of priority under 35 U.S.C. § 119 of Swedish patent application number 1651422-6 filed Oct. 28, 2016 and U.S. Provisional Patent Application Ser. No. 62/414,193 filed. Oct. 28, 2016.

BACKGROUND OF THE INVENTION

Field of the Invention

The present invention relates to the field of 3D bioprinting, bioinks for bioprinting, constructs and tissues prepared by bioprinting, as well as the medical use of such constructs and tissues for treatment in the field of tissue replacement or defect.

Description of Related Art

There is an unmet medical need for novel procedures for repair of larger bone defects. Bone has in contrast to cartilage, a very good healing capability but larger defects cannot be repaired without transplantation of autologous graft or support material. One example can be a reconstruction of the mandible due to traffic accidents, or cancer. The most common cancer affecting the mandible is squamous cell carcinoma. According to Cancer Research UK, in 2012 61,400 cases of oral cavity cancer were reported in Europe [1]. 28,260 cases were reported in 2014 in the United States of America [2]. The most common current solution is transplantation of fibula graft which entails a number of other complications such as problems with covering large soft tissue defects. Other solutions can be titanium plates or allogenic bone grafts. These solutions also have many disadvantages such as titanium plates being exposed through the skin. Furthermore, the current solutions are painful for the patients and they are also very expensive and time consuming for doctors and patients.

Bone, a structural element of human body, also known as hard tissue is composed of inorganic phase, which is hydroxyapatite, Collagen I fibrils and proteoglycans. There are several cell types which are involved in bone building process. The most important are osteoblasts which produce Collagen I which is organized into hierarchical structure. Other cells such as osteoclasts are involved in bone remodeling process which involves resorption of inorganic phase. Inorganic phase often called mineral phase is not directly synthesized by cells but crystallized in the microenvironment created during bone formation process called also osteogenesis. When large defects have to be repaired the guidance of cells is necessary and this can be provided by grafting of bone from another site or placing biomaterial. Both biodegradable polymeric materials and inorganic materials have been used for many years as synthetic bone graft or scaffold materials.

Hydroxyapatite has a crystalline structure and exists in bone tissue as whiskers. As a crystallite it is very slowly solubilized. Tri-calcium phosphate (TCP) is an inorganic material which is used for dental and bone repair applications. Two forms of TCP are existing; $\alpha$-TCP and $\beta$-TCP. $\alpha$-TCP resorbs faster than $\beta$-TCP. TCP exhibits properties which make it suitable as dental filler or bone filler since material when resorbed provides Calcium and Phosphate ions which are necessary for formation of hydroxyapatite which is main component of bone. During the resorption process the voids are formed which can be replaced by growing bone. One of the challenges when using TCP inorganic particles is to fuse them into 3D structure or made them injectable. Porous calcium phosphate bone material converted into self-setting material is for example described in U.S. Pat. No. 8,147,860 B2 [3]. The field of that invention is bone repair and replacement. There are many commercially available TCP materials on the market and some of them have been processed to be injectable. For in situ hardening $\beta$-TCP known as Easy-graft® from Sunstar Americas Inc is coated with poly(lactic-co-glycolic acid) and is used together with BioLinker and it has shown good performance for Alveolar Ridge preservation [4]. Processability of TCP remains however major challenge.

When large bone cavities have to be replaced by growing bone there is a need for many cells to be there and be productive. Placing of empty scaffold relies only on migration process of stem cells and their differentiation. Many scientists have studied use of mesenchymal stem cells derived from bone marrow or adipose tissue and their differentiation into osteoblasts. Use of TCP materials is very attractive in such applications [5]. Scientists have shown that the presence of TCP can stimulate differentiation process of stem cells [6]. New technology is necessary to utilize TCP together with cells for repair of large bone cavities.

3D Bioprinting is an emerging technology which has found applications in production of almost every industrial product. The advantage of 3D printing technology is bottom up fabrication process in which layer by layer of material are deposited and fused. Any 3D object can be designed or scanned and transferred into CAD file which is then converted to printer driving format such as for example stl file and desired 3D object can be built. There are already several applications of 3D Printing technology for production of patient specific implants. One of the great advantages of 3D Printing is the ability to produce a highly porous structure which is advantageous when implanted since tissue integration and vascularization can take place. TCP materials can thus be 3D printed with different binders to make patient specific scaffolds which could be ideal for bone healing. For large cavities, however there is a need for large amount of cells in order to accelerate healing process.

3D Bioprinting technology is related to 3D printing by being an additive manufacturing technology but it has been developed to be able to print with cells and thus fabricate tissue and organs. 3D Bioprinting has a potential to revolutionize medicine and health care. In a typical 3D Bioprinting setting cells can be deposited by one printing head and supporting material also called bioink can be dispensed by another printing head. There are several functions of bioink; to provide support and protection for cells during printing process, to provide suitable rheological properties which will result in high fidelity of the construct and to provide good mechanical properties to the construct. After bioprinting operation the process of tissue growth is starting. This includes cell migration, cell adhesion, cell proliferation, cell differentiation and depositing of extracellular matrix by the cells. In all those cell fate processes the bioink which after bioprinting become a scaffold plays crucial role.

Recently researchers found out that it is advantageous to mix cells together with bioink to produce cell laden bioink. The hydrogels are most suitable for such applications since they bind lots of water and thus provide for the cells suitable environment. Different polymer forming hydrogels have been evaluated as bioinks for 3D Bioprinting process. Among these natural polymers such as alginates, hyaluronic acid, agarose, chitosan and collagen have been mostly studied. The major limitation of all these hydrogels is the rheological properties. All polymer solutions are shear thinning which means that they have lower viscosity at higher shear rate. But this is not sufficient to provide very high printing fidelity which is defined as thin lines which can stay at the same dimension without sagging.

Cellulose nanofibrils are biosynthesized by most plants as structural elements. They have typically 5-20 nm diameter and can be micrometers long. During the cell wall assembly process they are incorporated into complex structure composed of other polysaccharides (hemicelluloses) and in the case of secondary cell wall also with lignin. Such composite structure can be disassembled using chemical processes and then cellulose nanofibrils can be isolated using a mechanical homogenizer. Such isolated cellulose nanofibrils are very hydrophilic and have very high surface area. They form hydrogels already at low solid content (2-3% dry matter). They are extremely shear thinning but in contrast to typical polymer solution they have very high low shear viscosity which is ideal property for a bioink. They can be printed with extrusion head or inkjet head and exhibit very high printing fidelity [7]. Cellulose nanofibrils can also be produced by bacteria. After the purification process which removes all bacteria and their debris cellulose nanofibrils show excellent biocompatibility [8]. Biomaterials based on bacterial cellulose nanofibrils have received several FDA approvals and can be found today in clinical applications such as dura repair membrane.

3D Bioprinting has great potential for bone repair. A good example of promising applications has been recently published [9] [10]. With suitable bioinks, 3D Bioprinting technology can soon find applications in clinic to repair large bone defects and the present invention may have major contribution in translation of 3D Bioprinting technology towards bone repair.

SUMMARY OF THE INVENTION

The present invention describes preparation of bioinks based on cellulose nanofibrils hydrogels with Calcium containing particles and their use for 3D Bioprinting of implantable devices with or without cells to heal large bone defects. Such bioinks can also be used for fabrication of model bone tissue.

These are the steps involved in the preparation of bioink, 3D Bioprinting and implantation of the construct to heal bone defect:
  Calcium containing powder, preferably Tricalcium Phosphate (TCP) and ideally β-TCP, or natural bone powder of human or porcine origin, is grinded into particles smaller than 400 microns or preferably smaller than 200 microns. Grinded particles are sterilized by heat or electron beam irradiation. Other sources of calcium-containing particles, or powder, can be used, such as hydroxyapatite.
  Cellulose nanofibril dispersion with dry matter between 2-3% by weight is sterilized by electron beam and mixed aseptically with crosslinkable biopolymer solution. Alginate or tyramine derived hyaluronic acid, fibrinogen with thrombin (to form fibrin), gelatin methacrylate or collagen methacrylate can be used as crosslinkable biopolymer.
  Calcium containing powder is mixed with cellulose nanofibril based dispersion and additional biopolymer. The ratio between inorganic phase and organic polymer phase depends on particle size of grinded mineral component. The concentration of the calcium containing powder can vary between 1% and 40% (w/v).
  The bone defect is scanned with MRI, CT or optical scanner.
  CAD file is prepared based on scan, and prepared taking into account the size, place, location, and other relevant factors relating to implantation.
  The construct with suitable porosity is 3D Bioprinted using Calcium containing nanocellulose fibril bioink and CAD file and implanted into the defect.
  The construct can be 3D Bioprinted with cells.
  Mesenchymal stem cells can be isolated from patient's bone marrow or adipose tissue.
  Cells are combined with Calcium particle filled nanocellulose fibril based bioink, preferably in an automated aseptic device, and transferred to a 3D Bioprinter, preferably in said operating room
  The construct can be printed with cell-laden Calcium particle filled nanocellulose fibril bioink.
  A coaxial needle can be used where the core can be printed with Calcium particle filled nanocellulose bioink and the shell can be printed with cell laden nanocellulose bioink
  The architecture and design and components of the 3D Bioprinted construct provide a robust, stable structure, biocompatibility, and the ability to be vascularized and become a high quality bone tissue.
  The patient is provided with a construct which will induce bone formation and thus repair large defect.

More specifically, the present invention relates to the following aspects:

In one aspect, the invention relates to cellulose nanofibril based bioink for use in 3D bioprinting, wherein the bioink comprises calcium containing particles, wherein the calcium-containing particles have a fraction size smaller than 400 microns. Preferably, the calcium-containing particles are in the form of synthetic β-tricalcium phosphate, single-phase hydroxyapatite, biphasic HA-TCP, or natural bone powder, preferably of human or porcine origin. According to one embodiment, the calcium containing particles have a fraction size smaller than 200 microns. Calcium containing particles with a "fraction size smaller than 400 microns" are calcium containing particles, or calcium containing powder, which, essentially do not include any particles larger than 400 microns, e,g, as determined by sieving particles after grinding. One reason for limiting the size of the particles is to keep resolution during bioprinting, i.e. with particles that are larger than 400 microns the resolution is negatively affected.

In another embodiment at least one additional biopolymer is added to the bioink, wherein the biopolymer is chosen from the group comprising alginates, hyaluronic acid and it derivatives, agarose, chitosan, fibrin, collagen and gelatin and their derivatives. Additional biopolymers are added to the bioink for cross-linking purposes and/or to contribute to rheological properties as hydrogels.

In another aspect, the invention relates to a method for preparing 3D bioprinting constructs that are suitable for use in implants to repair dental defects or bone defects in the human or animal body comprising the steps of:
 a) providing the cellulose nanofibril based bioink according to above;
 b) optionally providing suitable living cells;
 c) mixing the components of step a) and b) and printing the construct(s) with a bioprinter apparatus;
 d) optionally incubating the construct in an environment suitable for the cells in the construct to differentiate.

The 3D bioprinted construct can e.g. be in the form of a grid or the like. The bioprinter apparatus can be of any commercially available type, such as the 3D Bioprinter INKREDIBLE from CELLINK AB. An example of "an environment suitable for the cells in the construct to differentiate" is disclosed in Example 2, but the conditions and reagents used may of course differ for different cell types. A skilled person in the art would be aware of suitable conditions for different types of cells, In one embodiment, the resulting 3D bioprinting construct is used for drug discovery applications or as a disease model, or for other research purposes.

In yet another embodiment, the cellulose nanofibril is provided by one of the following alternatives: biosynthetization by bacteria, isolation from wood, isolation from primary cell wall or isolation from tunicates.

In a further embodiment, a coaxial needle is used in the bioprinter apparatus for printing the construct(s), whereby a core is printed with calcium particle filled cellulose nanofibril bioink and a shell is printed with cell-laden cellulose nanofibril bioink. Thus according to another aspect, a 3D bioprinted construct is provided, wherein said construct is prepared according to above, comprising a core and a shell, wherein the core comprises the bioink according to the above, and the shell comprises the bioink according to the above comprising suitable living cells.

In yet another aspect, the invention relates to a 3D bioprinted construct that are suitable for use in implants to repair dental defects or bone defects in the human or animal body composed of cellulose nanofibril bioink comprising calcium phosphate particles with a fraction size smaller than 200 microns, optionally at least one additional biopolymer, and optionally living cells.

In a further aspect, the invention relates to a 3D bioprinted construct that are suitable for use in implants to repair dental defects or bone defects in the human or animal body prepared by the method for preparing 3D bioprinting constructs according to the invention.

In one embodiment relating to all aspects of the invention, the living cells are mesenchymal stem cells that are differentiated into osteoblasts in the constructs. Also, chondrocytes can be differentiated into osteoblasts, as well as induced pluripotent stem cells (iPS cells).

In yet another embodiment, the living cells are osteoblasts.

In still another aspect, the invention relates to a method for implanting 3D bioprinting constructs to repair dental defects or bone defects in the human or animal body comprising steps a)-e) according to the method for preparing 3D bioprinting constructs according to the invention, and
 f) implanting the construct in a human or animal body in order to repair a dental defect or a bone defect, wherein
   i. a construct comprising living cells is used for repairing a bone defect by creating living bone tissue, and
   ii. a construct without living cells is used for repairing a dental defect.

In one further aspect the invention relates to a 3D bioprinted living bone tissue prepared by the method(s) of the invention. By "living tissue" is meant a tissue model with living cells. It may thus relate to a structure, such as a scaffold, with living cells attached to it, or living cells enclosed within the structure. The structure may be of organic or inorganic origin. The material of the structure may be any material that allows for living cells to survive and replicate.

In one embodiment, the tissue comprises living osteoblasts and wherein spaces between bioink printed grids allow diffusion of nutrients, oxygen, proteins and/or growth factors. Spaces between bioink printed grids are important to allow for e.g. vascularization. The size of the spaces should be at least about 10 microns.

In another embodiment, the living cells are osteoblasts that are cultured to build bone.

In still another aspect, the invention relates to 3D bioprinted living tissue for use in the treatment of an animal or human patient suffering from a tissue defect, lack of tissue or need for replacement of a tissue, wherein the 3D bioprinted living tissue is implanted in the tissue of the patient.

In one embodiment the tissue is chosen from bone or tooth.

In one further aspect, the invention relates to a method for treatment of an animal or human patient suffering from a tissue defect, lack of tissue or need for replacement of a tissue, wherein a 3D bioprinted living tissue of the invention is implanted in the tissue of the patient.

In one embodiment, the tissue is chosen from bone or tooth.

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

The present invention relates to materials based on cellulose nanofibrils based hydrogels with natural or synthetic Calcium containing particles such as Tri-calcium Phosphate or bone powder and their use as 3D Bioprinting bioinks to repair dental or bone defects. The bioinks based on cellulose nanofibrils hydrogels filled with Calcium containing particles can be used as bioinks in 3D Bioprinting process with or without human or animal cells. Such bioprinted constructs can be implanted in bone defects to promote bone healing process.

The advantage of using cellulose nanofibril hydrogels is extreme shear thinning properties which is crucial for high printing fidelity. High printing fidelity makes it possible to bioprint porous structures which can be spontaneously vascularized upon implantation. Vascularization is a key to promote bone healing process since vascularization makes it possible for oxygen and nutrient transport. In addition, the cells can migrate through porosity to enhance bone formation process. Another advantage of using cellulose nanofibrils is their large surface area and hydrophilic properties which make them an excellent binder and dispersing agent for organic and inorganic particles.

Bioinks described in this invention have very good mechanical properties and excellent biocompatibility. The good integrity of the structures bioprinted with bioinks based on cellulose nanofibrils with Calcium particles provide very good support for another structure of cell laden hydrogel which can be biofabricated with coaxial needle. Autologous cells can be used including mesenchymal stem cells isolated from bone marrow or adipose tissue or osteoblasts. Calcium ions and phosphate ions, with native or synthetic origin which are in the particles within printed constructs will be resorbed and will induce osteogenesis process which is a key process in bone formation. Such bioprinted constructs with or without cells are very efficient in repair of larger bone defects. Critical size defects cannot be bridged by naturally regenerated bone. Cellulose nanofibrils with different origin can be used in the bioinks. They can be produced by bacteria or isolated from wood or annual plants, such as from primary cell walls, or isolated from tunicates. They can be neutral or charged. They can be oxidized and thus biodegradable. The key characteristic of Calcium particles is their size in order to be used as component of bioink in 3D Bioprinting process. Large agglomerates above 200 micron can block the printer nozzle which will result in clogging. The present specification describes how particles should be selected and prepared to be used in bioink, the process of bioink fabrication, 3D Bioprinting with different nozzles and applications with and without cells for repair of large bone defects.

The β-tricalcium phosphate (β-TCP) particles can be obtained from various sources, e.g. from DePuy Synthes (chronOS Bone Graft Substitute). The natural bone powder can be of e.g. human or porcine origin. Typically, the material is provided in sterile and gamma-irradiated form. E.g. the natural bone powder is obtained from LifeNet Health (ReadiGraft Demineralized Cortical Particulate with grind size 125-1000 microns). The powder can be sieved before use to obtain the desired particle size.

For mixing the cellulose nanofibrils and the calcium phosphatase particles, the sterile bioink components are placed inside a sterile syringe with male luer lock. A sterile-packaged female-female Luer lock connector is used to connect both syringes at the male luer connection. This process for mixing is ideal for transferring and mixing low viscosity solutions. The bioink components are mixed by moving the contents of the syringes from one syringe to the other until a homogenous mixture is obtained. This process ensures maximum sterility by facilitating a contamination-free handling, since it is a closed system, and it reduces residual waste in the syringes.

EXAMPLES

To facilitate a better understanding of the present invention, the following examples of certain aspects of some embodiments are given. In no way should the following examples be read to limit, or define, the scope of the invention.

Example 1

Preparation and Evaluation of Bioinks

Figure 1:
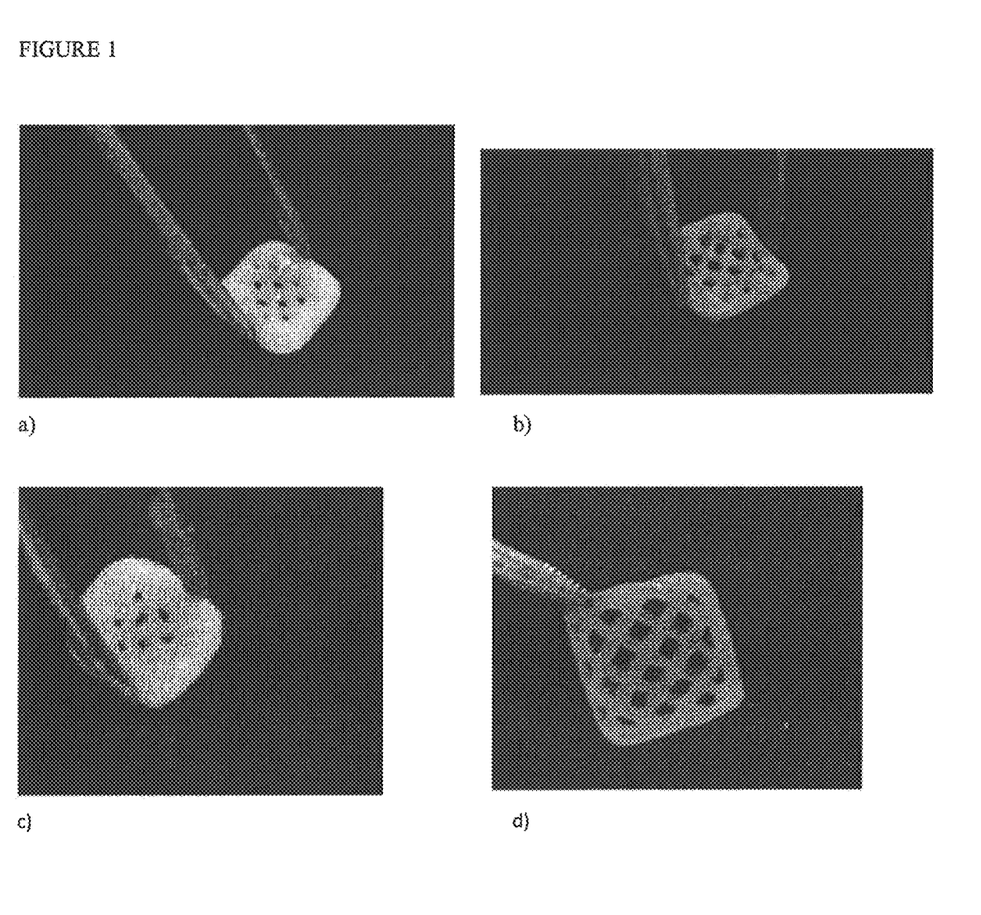
FIG. 1 is showing printed constructs based on Calcium Phosphates from various sources and various composition of bioinks. a) 18% Bone powder (Bio-Oss) b) 10% β-TCP coated with poly(lactic-co-glycolic acid) c) 20% porous hydroxyapatite derived from red marine algae d) 20% synthetic β-TCP
Figure 2:
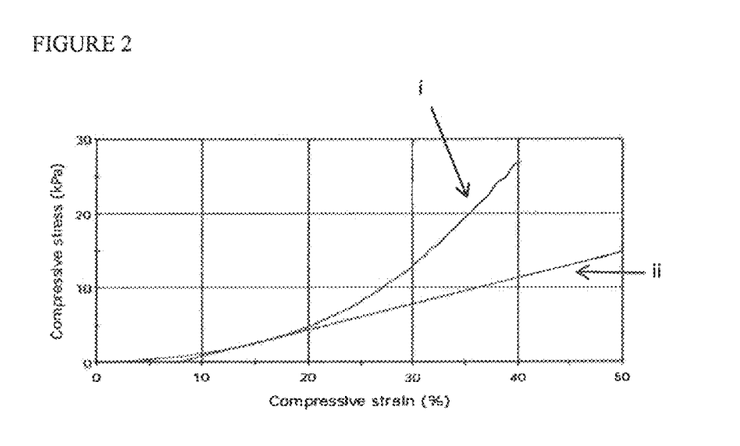
FIG. 2 is showing results of the mechanical testing of cellulose nanofibrils/TCP printed constructs.

Granules of β-tricalcium phosphate (β-TCP) 1.4-2.8 mm particle size were grinded in a mechanical grinder to a powder and finally homogenized using a hydraulic press. Other Calcium phosphates from different sources were compared. The grinding process was designed to provide the size of the particles to be below 200 microns as determined by sieving process. Nanocellulose fibril hydrogel was prepared by homogenization of Bacterial Cellulose pellicle which was purified according to protocols published elsewhere [8]. Cellulose nanofibrils isolated from wood have also been evaluated. In order to provide good crosslinking, between 10-20% of alginate based on dry weight of cellulose nanofibrils was added. A typical bioink without mineral phase contains between 2-3% dry weight cellulose nanofibrils and alginate mixture. Different mixing devices were tested. FIG. 1 shows a mixing device which is constructed by combining two cartridges. Mixing was achieved through movement of the pistons in the individual cartridges, as described above. Several different compositions of mineral bioinks were prepared and evaluated by measuring rheological properties, mechanical properties and printability. Calcium Phosphates from different suppliers were also evaluated. Before printing, the mixtures with different ratios of Calcium Phosphates and nanocellulose bioink were prepared and evaluated with regard to rheological properties. The best combinations with regard to flow properties at pressures below 120 kPa were selected. After mixing the cartridge of Calcium particle filled nanocellulose bioink was placed in a 3D Bioprinter INKREDIBLE from CELLINK AB, Sweden and the grid was printed. FIG. 1 compares the structure of printed grids of the same based on bioinks with different compositions. Figure a a) shows the construct printed with bioink containing 18% w/v Bone substitute (Bio-Oss). It can be seen that printing fidelity is not very good. FIG. 1b) shows construct printed with 10% w/v β-TCP coated with poly(lactic-co-glycolic acid). Printing fidelity is not very good probably because polymer coating protect 1-TCP particles and dispersing in bioink is not very efficient. FIG. 1c) shows construct printed with 20% porous hydroxyapatite derived from red marine algae. Printing fidelity is very poor. FIG. 1d) shows constructs printed with bioink containing 20% synthetic β-TCP. It shows excellent printability with very high fidelity. This combination was selected for further studies. FIG. 2 shows evaluation of biomechanical properties using unconfined compression testing. Compression testing was performed on casted discs prepared from the four ink formulations seen in Table 1. By using a positive displacement pipet (Microman, Gilson, USA) and casting units (Q-Gel bio, Lausanne, Switzerland), discs were casted by dispensing 75 µL of bioink onto a casting plate and covering the dispensed drop with a top plate. The casting units with the discs (8 mm×1.5 mm) were cross-linked in a bath of 90 mM CaCl2 (Sigma-Aldrich) for 10 min and then immersed in HyClone Basal Medium Eagle (Sigma-Aldrich) for 48 h at room temperature. After cross-linking and equilibration in medium, the discs had a diameter of 8 mm and a thickness of 1.2 mm on average. Initial dimensions of the discs were measured with a digital caliper. A universal testing machine (Instron Model 5565A, UK) equipped with a 100 N load cell was used for the unconfined compression test, which was performed in wet conditions at room temperature. The strain rate was set to 10%/s, and the samples were compressed until 40% compressive strain. Bluehill software (Instron) was used to calculate the compressive stress and strain, compressive stiffness (tangent modulus) at 30% strain, and compressive stress at 30% strain for all samples (n=6 per group). As shown in the graph of FIG. 2, the addition of β-TCP to nanocellulose fibril bioink (i) results in increased compression strength and stiffness, and hence a higher mechanical strength, as compared to the bioink without β-TCP (ii).

Example 2

3D Bioprinting of Implantable Constructs

Figure 3:
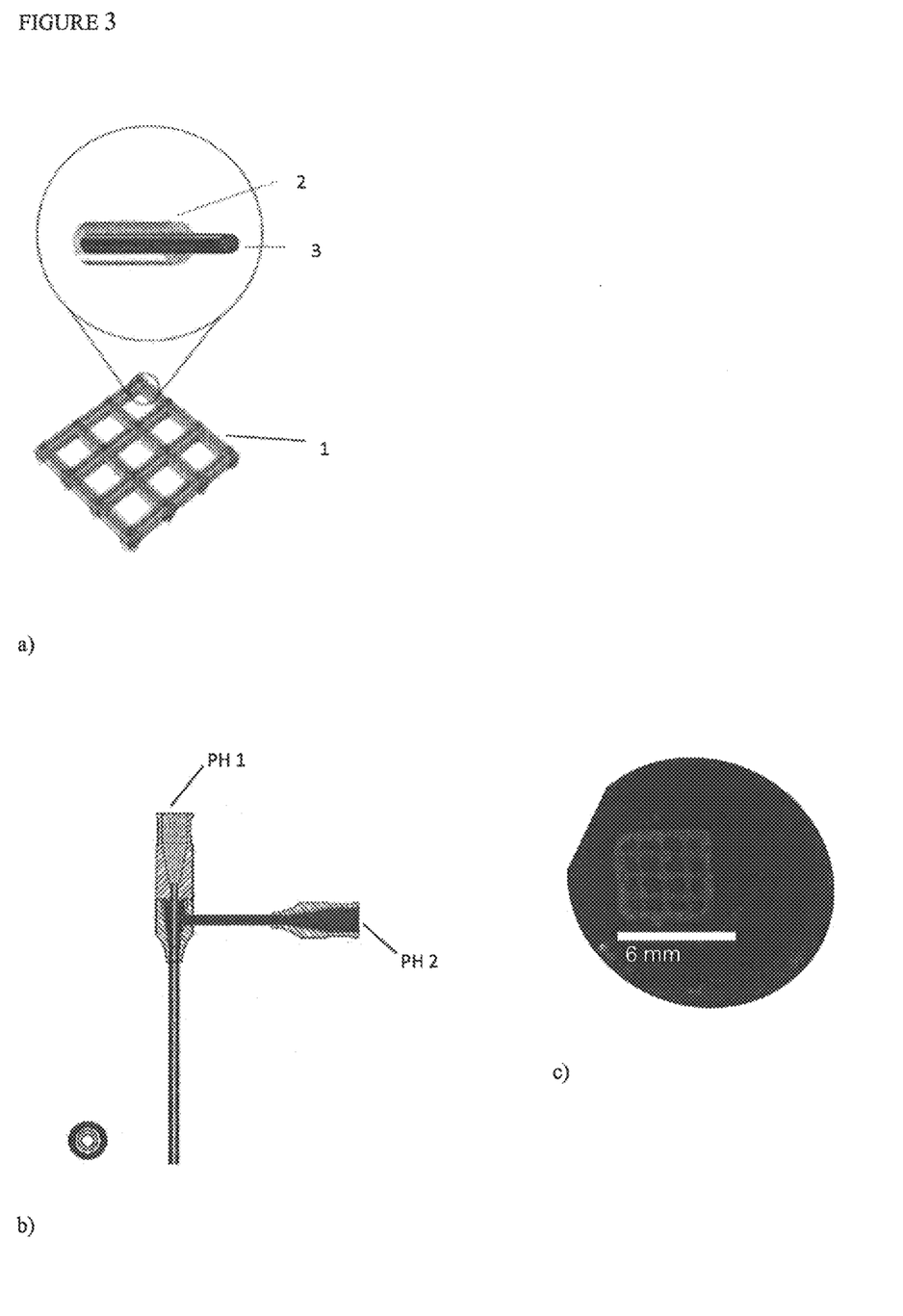
FIG. 3 shows design of a core-shell construct (a), a schematic picture of the coaxial needle (b) used in experiment where the core is composed of cellulose nanofibril/20% TCP bioink and the shell is nanocellulose bioink with mesenchymal stem cells, and a photograph (c) of a construct produced in said experiment.

Very high viscosity of Calcium filled bioinks resulted in much higher pressure necessary to get printed constructs. In order to use bioinks with cells the core shell structures (1) were designed as shown in FIG. 3a. One possible design is to use Calcium filled bioink as a core and cell filled nanocellulose bioink as a shell. In FIG. 3a, the structure 1 comprises an outer shell 2 and an inner core 3. The outer shell may contain nanocellulose bioink and mesenchymal stem cells, and the inner core 3 may contain 20% β-TCP/ nanocellulose bioink. Opposite can be also printed. In order to be able to print such structures coaxial needle is installed, see FIG. 3b. The bioink of the inner core is introduced at PH 1, and the bioink of the outer shell is introduced at PH 2. Prior to bioprinting nanocellulose bioink in DMEM medium solution was prepared. Confluent human adipose derived mesenchymal cells AD-MSCs were washed with 6 mL DPBS and then incubated with 6 mL of TrypLE at 37 degree. Progress of cell detachment was evaluated using a confocal light microscope. TrypLE activity was quenched by adding 6 mL of spent media to the culture flask. The cell solution was transferred to a 15 mL centrifuge tube and centrifuged at 200 g for 5 min. The supernatant was aspirated and the cells were resuspended in 200 microL of DMEM and mixed with 2% nanocellulose dispersion to obtain a concentration of $2 \times 10^6$ cells per mL in the bioink. For the bioprinting, 20% O-TCP nanocellulose bioink was inserted into printer head 1 (PH 1) and the cell-laden bioink was inserted into printer head 2 (PH 2). Pressures of 105 kPa (PH 1) and 55 kPa (PH 2) were applied. Grids of 6×6 (line space of 2 mm) consisting of 2 layers were printed and subsequently cross-linked for 6 min using 100 mM $CaCl_2$. They were then transferred to osteogenic medium and incubated at 37 degree and 5% CO2. The medium was exchanged every 2-3 days. BMP-2 treatment was started at day 4.

Figure 4:
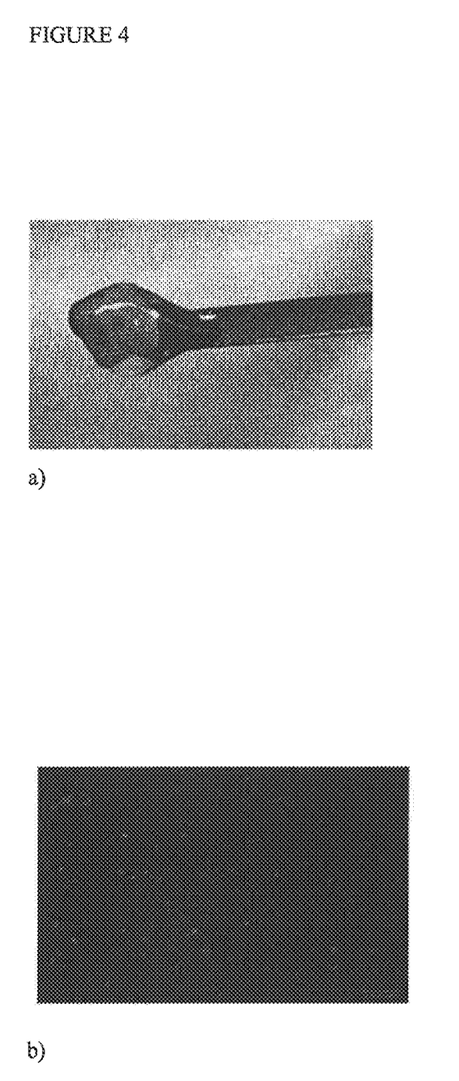
FIG. 4 is showing a 3D Bioprinted core-shell construct during cultivation in vitro (a) and results of cell viability after 3 days (b), wherein light spots represent cells which are alive and dark spots the dead cells. The cell viability is more than 90%.

The staining was performed using LIVE/DEAD Cell Imaging Kit from ThermoFisher Scientific, USA. The cell laden bioinks were washed in serum-free osteogenic medium for 30 minutes at 37 degree. The live/dead staining solution was mixed at a ratio of 1:2 with serum-free osteogenic medium, i.e. 2 mL of staining solution with 4 mL of medium. The media was then removed from the constructs and 450 mL of staining solution were added instead, making sure that the entire construct is covered. They were then incubated for one hour at 37 degree C. The staining solution was removed from the constructs and was replaced with 450 mL of serum-free osteogenic medium for one hour at 37 degree C. in order to wash the constructs. The medium was replaced with fresh medium after 30 minutes. The medium was then replaced with Live Cell Imaging Solution and the samples were imaged using confocal fluorescence microscopy with FITC (live) and Texas Red (dead) filters at 10× magnification. FIG. 4b, wherein light spots represent living cells and dark spots represent dead cells, shows high cell viability. The construct is ready for implantation after 28 days of differentiation in vitro. It is also possible to directly implant cell free construct or cell filled construct.

Example 3

3D Printing Using Human Bone Powder as a Source

Example 1 and 2 is repeated using human bone powder (LifeNet Health (ReadiGraft Demineralized Cortical Particulate with grind size 125-1000 microns)) instead of the other materials of Example 1 and 2. The powder is sieved before use to obtain the desired particle size (less than 400 microns, or less than 200 microns). The human bone powder is used with the same parameters as for the β-TCP-particles. The same, promising results are expected, i.e. excellent printability with high fidelity.

REFERENCES

[1] Oral cancer statistics. Retrieved from http://www.cancerresearchuk.org/health-professional/oral-cancer-statistics #heading-Zero on 2016 Mar. 6.
[2] Achilleas Thoma, Carolyn Levis, and JEM Young. Oromandibular reconstruction after cancer resection. Clinics in plastic surgery, 32(3):361-375, 2005.
[3] Aron D. Rosenberg, Laurent D. Gillès de Pélichy, Shrikar Bondre, Michael Strunk, 2005, U.S. Pat. No. 8,147,860 B2
[4] MD Leventis et al Minimally Invasive Alveolar Ridge Preservation Utilizing an In Situ Hardening 1-Tricalcium Phosphate Bone Substitute: A Multicenter Case Series, International Journal of Dentistry, Volume 2016 (2016), Article ID 5406736
[5] Robert A Horowitz, Ziv Mazor, and Christian Foitzik. ß-tricalcium phosphate as bone substitute material: properties and clinical applications. The International Journal of Dental Implants & Biomaterials, pages 2-11, 2009.
[6] Christian Weinand, Irina Pomerantseva, Craig M. Neville, Rajiv Gupta, Eli Weinberg, Ijad Madisch, Frederic Shapiro, Harutsugi Abukawa, Maria J. Troulis, and Joseph P. Vacanti. Hydrogel-Beta-TCP scaffolds and stem cells for tissue engineering bone. Bone, 38(4):555-563, 2006.
[7] Markstedt, K., A. Mantas, I. Tournier, H. M. Avila, D. Hagg, and P. Gatenholm, 3D Bioprinting Human Chondrocytes with Nanocellulose-Alginate Bioink for Cartilage Tissue Engineering Applications. Biomacromolecules, 16(5): p. 1489-1496, 2015.
[8] Martinez Avila, H.; Schwarz, S.; Feldmann, E.-M.; Mantas, A.; von Bomhard, A.; Gatenholm, P.; Rotter, N. Appl. Microbiol. Biotechnol. 2014, 98, 7423-7435.
[9] Hyun-Wook Kang, Sang Jin Lee, In Kap Ko, Carlos Kengla, James J Yoo, and Anthony Atala, 3D bioprinting system to produce human-scale tissue constructs with structural integrity. Nature biotechnology, 34(3):312-319, 2016.
[10] Natalja E Fedorovich, Joost R De Wijn, Abraham J Verbout, Jacqueline Alblas, and Wouter JA Dhert. Three-dimensional fiber deposition of cell-laden, viable, patterned constructs for bone tissue printing. Tissue Engineering Part A, 14(1):127-133, 2008.

The invention claimed is:

1. A bioink for use in 3D bioprinting, wherein the bioink is suitable for use with living cells and consists essentially of a cellulose nanofibril based hydrogel; a biopolymer selected from the group consisting of: alginates, hyaluronic acid, agarose, chitosan, fibrin, collagen, and gelatin; and 1-40% (w/v) calcium-containing particles, wherein the calcium-containing particles have a fraction size smaller than 400 microns and consist essentially of β-tricalcium phosphate, biphasic HA-TCP, or natural bone powder.

2. The bioink according to claim 1, wherein said calcium-containing particles have a fraction size smaller than 200 microns.

3. The bioink according to claim 1, wherein the natural bone powder is of human or porcine origin.

4. The bioink according to claim 1, wherein the cellulose nanofibril is provided by one of the following alternatives: biosynthetization by bacteria, isolation from wood, isolation from primary cell wall or isolation from tunicates.

5. A cellular bioink composition comprising the bioink of claim 1 and living cells.

6. The cellular bioink composition according to claim 5, wherein the living cells are mesenchymal stem cells, osteoblasts, or induced pluripotent stem cells (iPSC).

7. A method for preparing a 3D bioprinting construct that is suitable for use in implants to repair dental defects or bone defects in a human or animal body comprising:
   a) providing a bioink according to claim 1, and
   b) printing a construct with the bioink and a bioprinter apparatus.

8. A method for preparing a 3D bioprinting construct that is suitable for use in implants to repair dental defects or bone defects in a human body or animal body comprising:
   a) providing a bioink of claim 1,
   b) providing living cells,
   c) mixing the components from a) and b) to obtain a cellular bioink composition,
   d) printing a construct with the cellular bioink composition of c) and a bioprinter apparatus, and
   e) optionally incubating the construct of d) in an environment suitable for cells in the construct to differentiate.

9. A 3D bioprinted construct prepared by the method according to claim 8.

10. The 3D bioprinted construct of claim 9, wherein a coaxial needle is further used in the bioprinter apparatus for printing the construct, and wherein the construct comprises a core and a shell, wherein
   (i) the core comprises the bioink of a) and the shell comprises the cellular bioink composition of d); or
   (ii) the core comprises the cellular bioink composition of d) and the shell comprises the bioink of a).

11. The 3D bioprinted construct of claim 9, wherein the living cells are mesenchymal stem cells that are differentiated into osteoblasts in the constructs, or wherein the living cells are osteoblasts or induced pluripotent stem cells (iPSC).

12. The 3D bioprinted construct according to claim 9, wherein the construct is an implant suitable to repair dental defects or bone defects in a human or animal body.

13. The 3D bioprinted construct according to claim 9, wherein the construct is suitable for use in drug discovery or as a disease model.

14. A method for repairing a bone defect in a human or animal body, comprising implanting in the body in need thereof the construct of claim 12, wherein living bone tissue is created.

15. A 3D bioprinted living bone tissue prepared by the method according to claim 14.

16. The 3D bioprinted living bone tissue according to claim 15, wherein the tissue comprises living osteoblasts and wherein spaces between bioink printed grids allow diffusion of nutrients, oxygen, proteins and/or growth factors.

17. The 3D bioprinted living bone tissue according to claim 15, wherein the living cells are osteoblasts that are cultured to build bone.

18. A method for treatment of an animal or human patient suffering from a tissue defect, lack of tissue or need for replacement of a tissue, comprising implanting in the tissue of the patient the bioprinted living tissue of claim 15.

19. The method for treatment according to claim 18, wherein the tissue is chosen from bone or tooth.

20. A method for repairing a dental defect in a human or animal body, comprising implanting into the body in need thereof a construct prepared by the method of claim 7.

21. The bioink according to claim 1, wherein the cellulose nanofibril and alginate are in a concentration of 2-3% based on the dry weight of the bioink.

* * * * *